United States Patent [19]

Diercks et al.

[11] Patent Number: 5,985,786
[45] Date of Patent: Nov. 16, 1999

[54] PACKED SILVER-CATALYST BED DOPED WITH PHOSPHORUS

[75] Inventors: Rainer Diercks, Neuhofen; Bernhard Knuth, Ludwigshafen; Albrecht Aicher, Frankenthal, all of Germany

[73] Assignee: BASF Aktiengesellschaft, Ludwigshafen, Germany

[21] Appl. No.: 09/117,538

[22] PCT Filed: Feb. 10, 1997

[86] PCT No.: PCT/EP97/00601

§ 371 Date: Aug. 5, 1998

§ 102(e) Date: Aug. 5, 1998

[87] PCT Pub. No.: WO97/30014

PCT Pub. Date: Aug. 21, 1997

[30] Foreign Application Priority Data

Feb. 13, 1996 [DE] Germany .............................. 196 05 212

[51] Int. Cl.$^6$ .............................. B01J 27/14; B01J 20/34; B01J 23/02; B01J 23/48
[52] U.S. Cl. .............................. 502/208; 502/34; 502/38; 502/56; 502/344; 502/347; 502/353
[58] Field of Search ..................... 502/208, 344, 502/347, 353, 34, 56, 38

[56] References Cited

U.S. PATENT DOCUMENTS 4,235,823  11/1980  Dudeck et al. ........................ 568/402
5,854,163  12/1998  Diercks et al. ............................. 502/56

FOREIGN PATENT DOCUMENTS 104666       4/1984   European Pat. Off. .
0 467 169    1/1992   European Pat. Off. .
WO 96/28249  9/1996   WIPO .

*Primary Examiner*—Mark L. Bell
*Assistant Examiner*—Patricia L. Hailey
*Attorney, Agent, or Firm*—Oblon, Spivak, McClelland, Maier & Neustadt, P.C.

[57] ABSTRACT

A phosphorus-doped silver catalyst fixed bed is obtainable by

I. arranging silver crystals obtained by electrolytic deposition of silver from an aqueous silver salt solution to form a starting silver catalyst fixed bed, II. producing an activated silver catalyst fixed bed from the starting silver catalyst fixed bed by passing through the latter, at from 150 to 800° C., a gas mixture comprising methanol and oxygen (gas mixture M), and III. bringing the activated silver catalyst fixed bed into contact with from 1 to 20,000 ppm by weight of phosphorus, based on the silver, in the form of a finely divided phosphorus compound having a melting point or decomposition temperature of more than 500° C. (phosphorus compound P).

9 Claims, No Drawings

PACKED SILVER-CATALYST BED DOPED WITH PHOSPHORUS

The present invention relates to a phosphorus-doped silver catalyst fixed bed obtainable by I. arranging silver crystals obtained by electrolytic deposition of silver from an aqueous silver salt solution to form a starting silver catalyst fixed bed, II. producing an activated silver catalyst fixed bed from the starting silver catalyst fixed bed by passing through the latter, at from 150 to 800° C., a gas mixture comprising methanol and oxygen (gas mixture M), and III. bringing the activated silver catalyst fixed bed into contact with from 1 to 20,000 ppm by weight of phosphorus, based on the silver, in the form of a finely divided phosphorus compound having a melting point or decomposition temperature of more than 500° C. (phosphorus compound P).

The invention further relates to a process for producing this and also a process for preparing formaldehyde using a phosphorus-doped silver catalyst fixed bed according to the present invention.

Silver catalysts which are suitable for the oxidation of methanol to give formaldehyde are generally known (cf. Ullmann's Enzyklopädie der technischen Chemie, 3rd edition, Urban und Schwarzenberg, Munich-Berlin, 1956, Volume 7, pp. 660 to 663). According to this process, silver is oxidized anodically in an electrolysis cell to form silver ions and these are again cathodically reduced to give silver. The coarsely crystalline silver formed at the cathode is suitable as catalyst for the synthesis of formaldehyde from methanol.

Advantageous effects which occur when using phosphorus compounds as promoters for the oxidation of methanol to formaldehyde in the presence of a silver catalyst are also known from CN-A-85 100 530, EP-A-0 467 169 and JP-A-38227/83.

EP-A-0 467 169 describes the production of a catalyst fixed bed built up of layers of silver crystals containing a pulverulent phosphorus-containing salt as promoter. In this process, the phosphorus-containing salt is applied to the silver catalyst before the silver catalyst is brought into contact with a hot gas mixture comprising oxygen and methanol.

However, the catalyst fixed beds described in that reference are in a modification of low activity immediately after application of the phosphorus-containing salt and transform only relatively slowly into a modification of high activity by means of which formaldehyde can be prepared in high yield and at a high conversion. This is associated with the following problems:

A catalyst fixed bed described in EP-A-0 467 169, which is used for the industrial production of formaldehyde in a generally customary, continuously operated plant, loses activity with time so that the yield drops. Therefore, to be able to operate the plant economically the used catalyst fixed bed has to be replaced by a fresh one after a certain operating time, for which purpose the synthesis process has to be interrupted. In order to subsequently restart the synthesis process, it is necessary to preheat the catalyst fixed bed to at least 360° C. so as to make available the activation energy required for the reaction. However, owing to the fact that the heat is rapidly given off because of the high surface area of the catalyst it is technically not simple to achieve such high temperatures. In practice, the catalyst fixed bed is heated, for example, by passing a hot inert gas stream (for example nitrogen or carbon dioxide) through the catalyst fixed bed and, when the catalyst has reached the required temperature, adding the gaseous reactants to the gas stream. Once the reaction has started and the catalyst has reached its full activity the heating of the catalyst fixed bed is no longer necessary since the oxidation of the methanol to formaldehyde is exothermic and the reaction zone, ie. the catalyst fixed bed, heats up to from 500 to 700° C. and thus has the minimum temperature required for the activation of the reaction. Since the catalyst fixed bed does not yet have its full activity immediately after the reaction starts, only small amounts of the reactants may be passed through the catalyst fixed bed at the beginning, since otherwise the reaction proceeds with little selectivity or there is even the danger of the catalyst fixed bed assuming a modification in which it is inactive. Only after about 30 hours has the catalyst fixed bed reached its full activity and the maximum amount of reactants per unit time can be passed over it.

Since during the activation phase, which is necessary to produce a catalyst fixed bed in a modification of high activity from that described in EP-A-0 467 169, the space-time yield is relatively low, there is a need for catalyst fixed beds which require a shorter activation phase to reach their final high-activity modification. In addition, the activation energy necessary for the reaction over the freshly produced catalyst fixed bed (ie. the minimum temperature which the catalyst fixed bed must have for the reaction to start) should be as low as possible.

It is an object of the present invention to provide a catalyst fixed bed which is simple to produce, makes possible the preparation of formaldehyde by oxidative dehydrogenation of methanol in high yield and with a high conversion and does not have the deficiencies described. In particular, the activation step which is generally carried out in the production plant for preparing formaldehyde should be as short as possible. Furthermore, the economical production of formaldehyde should be possible even during this time, so that the production stoppage necessitated by the replacement of the catalyst fixed bed is as short as possible.

We have found that this object is achieved by the phosphorus-doped silver catalyst fixed bed described in the introduction.

The preparation of the silver crystals described in step I is generally known (cf. Ullmann's Enzyklopädie der technischen Chemie, 3rd edition, Urban und Schwarzenberg, Munich-Berlin, 1956, Vol.7, pp. 660 to 663). Particularly good results are achieved using the starting catalyst fixed beds described in DE-A-23 22 757.

Suitable silver crystals are obtained, in particular, when the electrolysis is carried out according to the process described in the German patent 11 66 171.

The electrolyte used is preferably an aqueous silver nitrate solution. This silver nitrate solution generally has a pH of from 1 to 4 and contains from 1 to 5% by weight of silver. The pH is advantageously set using nitric acid.

Electrodes employed are those customarily used in the electrolysis of silver. Suitable anodes are sacks which have been charged with the silver to be oxidized, generally as granules or as powders. Suitable cathodes are, in particular, sheets of silver.

The electrolysis is advantageously carried out at current densities of from 80 to 500 A/m$^2$ of cathode area and electrolyte temperatures of from 10 to 30° C.

To achieve these current densities, voltages of from 1 to 15 volt are required in most electrolysis cells.

It is advisable to continually remove silver crystals formed from the cathode. In general, silver crystals having a particle size of from 0.2 to 5 mm are obtained.

A one-off electrolysis is usually sufficient to obtain usable silver crystals.

Such fixed beds, which are also referred to as "short beds", are generally known and described, for example in Ullmanns Encyklopädie der technischen Chemie, 4th Edition, Verlag Chemie, Weinheim-New York, Volume 13, pp. 539 to 541.

In general, the silver crystals are arranged to form a starting silver catalyst fixed bed comprising from 1 to 9 layers of silver crystals and having a total bed thickness of from 1 to 10 cm. Such silver catalyst fixed beds are known, for example, from DE-C-23 22 757, which are hereby fully incorporated by reference.

In step II, the starting silver catalyst fixed bed is activated by passing through it, preferably continuously, at from 100 to 800° C., preferably from 200 to 700° C., a gas mixture (M) comprising methanol and oxygen. The gas mixture generally contains from 0.25 to 0.60 mol, preferably from 0.35 to 0.50 mol, of oxygen per mol of methanol and from 0.2 to 3.0 mol, preferably from 0.67 to 1.75 mol, of water per mol of methanol and from 0.9 to 2.3 mol, preferably from 1.3 to 1.8 mol, of nitrogen per mol of methanol. To achieve the temperature defined according to the present invention it is advantageous to preheat the gas mixture to these temperatures at the commencement of the passing-through of the gas mixture. In general, the preheating of the gas mixture (M) becomes superfluous after a certain time, since the fixed bed is heated to the required temperature by the heat of reaction which is liberated.

The activation of the starting catalyst fixed bed is advantageously carried out in a fixed-bed reactor as is customarily used for the preparation of formaldehyde by oxidative dehydrogenation of methanol and the gas mixture (M) is passed continuously through this reactor. Preferably, the reactor is upright and the gas mixture (M) is passed through the reactor from the top downwards. Such reactors and processes are described, for example, in EP-A-467 169, DE-A-24 44 586 and EP-A-0 150 436, which are here incorporated in full by reference.

Advantageously, the cross-sectional area of the reactor and that of the starting silver catalyst fixed bed are selected so as to be the same and the fixed bed is arranged in the reactor so that the layers of the silver crystals are perpendicular to the flow direction of the gas mixture (M).

To produce the activated silver catalyst fixed bed, it is generally sufficient to pass from 0.0001 to 0.5 kg, preferably from 0.01 to 0.5 kg, of methanol in the form of the gas mixture (M) per $cm^2$ of cross-sectional area of the starting silver catalyst fixed bed at from 100 to 500° C., preferably from 200 to 700° C., through the starting silver catalyst fixed bed. The indicated amounts of the gas mixture (M) are advantageously passed through at a velocity which is generally selected such that the gas mixture (M) is passed through in from 0.01 to 500 hours, preferably from 0.1 to 100 hours, particularly preferably from 1 to 500 hours.

Even during the activation phase, the methanol present in the gas mixture (M) is converted virtually quantitatively into formaldehyde. This means that step II can also be utilized for the production of formaldehyde, even if the space-time yield is not yet quite as high as in the case of the phosphorus-doped silver catalyst fixed bed of the present invention.

In step III, the activated silver catalyst fixed bed is brought into contact with from 1 to 20,000 ppm by weight, preferably from 5 to 5000 ppm by weight, of phosphorus, based on the silver, in the form of a finely divided phosphorus compound having a melting point or decomposition temperature of more than 500° C. (phosphorus compound P).

Suitable phosphorus compounds (P) are phosphorus-containing salts. Examples of these are the phosphorus-containing salts mentioned in DE-A-4 022 603, eg. inorganic phosphates of alkali metals, alkaline earth metals and heavy metals such as Ag, Zn and Fe or of boron and ammonium.

Preference is given to phosphates or pyrophosphates of alkali metals or alkaline earth metals, eg. $Na_4P_2O_7$, $Li_3PO_4$, $Mg_3(PO_4)_2$, $Ca_3(PO_4)_2$.

In general, the procedure is to sprinkle a finely divided powder of the phosphorus compound (P) onto the activated silver catalyst fixed bed or to impregnate it with a solution of the phosphorus compound (P) and allow the solvent to evaporate.

The particle size of the phosphorus compound (P) used as powder is not critical, it is generally from about 1 mm to 1 $\mu$m.

The solutions of the phosphorus compounds (P) are generally aqueous solutions containing from 0.01 to 50% by weight of the phosphorus compound (P). To impregnate the activated silver catalyst fixed bed, it is soaked with one of these solutions or, particularly advantageously, the solutions are sprayed onto the activated silver catalyst fixed bed, and the solvent is subsequently evaporated.

The amount of phosphorus compound (P) sprayed on or sprinkled on is preferably selected such that the amount of phosphorus is from 0.01 to 100 mg, preferably from 0.05 to 10 mg, per $cm^2$ of cross-sectional area of the phosphorus-doped silver catalyst fixed bed.

It is advantageous not to interrupt the passing-through of the gas stream (M) while applying the phosphorus compound (P) to the activated silver catalyst fixed bed.

This procedure has the advantage that, if the production of the phosphorus-doped silver catalyst fixed bed is carried out in a fixed-bed reactor which is also suitable for the oxidative dehydrogenation of methanol to give formaldehyde, the preparation of formaldehyde from the gas mixture (M) using the phosphorus-doped silver catalyst fixed bed of the present invention can immediately follow the production of the latter. The gas mixture (M) used for activating the starting silver catalyst fixed bed usually has the same composition as that used for preparing formaldehyde from the gas mixture (M) using the phosphorus-doped silver catalyst fixed bed. In this way, it is possible to particularly efficiently combine the production of the phosphorus-doped silver catalyst fixed bed, during which formaldehyde can also be produced, with the production of formaldehye using the catalyst fixed bed of the present invention.

It is also possible to produce a phosphorus-doped silver catalyst fixed bed having maximum activity in an iterative process by, in step III, first applying only part of the phosphorus, advantageously from 0.01 to 2 mg, preferably from 0.05 to 1 mg, per $cm^2$ of the cross-sectional area of the activated silver catalyst fixed bed, to the latter in the form of the phosphorus compound (P) and increasing the amount of phosphorus compound (P) stepwise, for example in steps of from 1 to 100%, based on the amount initially applied, and simultaneously monitoring the yield of formaldehyde. The amount of phosphorus compound (P) applied is increased stepwise until no increase in yield can be achieved by further application of the phosphorus compound (P).

The phosphorus-doped silver catalyst fixed beds, like previously known silver catalysts, continually lose activity during use for preparing formaldehyde, which is made apparent by falling conversion and yields of formaldehyde.

This activity loss of the catalysts of the present invention can be partly avoided if in addition, either continuously or discontinuously (in each case 1 portion after introducing a defined amount of gas mixture (M)), from 0.01 to 100 ppm by weight of phosphorus, based on the phosphorus-doped silver catalyst fixed bed, is applied to the latter in the form of the phosphorus compound (P) per kg of methanol in the form of the gas mixture (M) which is passed through the phosphorus-doped silver catalyst fixed bed per 1 cm² of the cross-sectional area of the latter, without interrupting the introduction of the gas mixture (M). In the case of continuous application, the activity loss can be slowed down, in the case of the stepwise discontinuous application it can be partly reversed.

This further application of the phosphorus compound (P) can be carried out in the same way as described in step II for the production of the phosphorus-doped silver catalyst fixed bed.

If the further application of the phosphorus compound (P) is carried out discontinuously, the intervals between the further applications of the phosphorus compound (P) to the phosphorus-doped silver catalyst fixed bed are usually selected such that during this time not more than 500 kg, preferably from 1 to 5 kg, of methanol in the form of the gas mixture (M) are passed through the phosphorus-doped silver catalyst fixed bed per 1 cm² of the cross-sectional area of the latter, since otherwise the yield would drop too much in between.

The preparation process for formaldehyde by oxidative dehydrogenation of methanol using the catalyst fixed bed of the present invention is otherwise carried out in a manner known per se, by passing the gas mixture (M) at from about 500 to 750° C., in particular from 600 to 710° C., through the phosphorus-doped silver catalyst fixed bed. The process is generally carried out continuously at a pressure of from 0.5 to 2 bar, preferably from 0.8 to 1.8 bar. It is advantageous to allow the reaction gases leaving the catalyst zone to cool for a short time, eg. to from 50 to 350° C. The cooled gas mixture is then advantageously fed to an absorption tower in which the formaldehyde is scrubbed from the gas mixture by means of water. Specific, particularly advantageous variants of the generally known process for preparing formaldehyde, which can also be employed in the process of the present invention, are recommended in DE-A-24 44 586, DE-A-24 51 990, EP-A-0 083 427 and EP-A-0 150 436, whose subject matter is hereby incorporated by reference.

The use of the catalyst fixed bed of the present invention enables formaldehyde to be prepared particularly economically by oxidative dehydrogenation of methanol.

In particular, the methanol- and oxygen-containing gas mixture which is passed through the fixed bed at the commencement of the synthesis process to activate it only has to be preheated to a comparatively low temperature. Furthermore, the time required for the activaton is relatively short, so that overall the space-time yield of the process for preparing formaldehyde is higher.

EXAMPLE 1

A three-layer starting silver catalyst fixed bed having a diameter of 15 cm and a total bed thickness of 2 cm was installed in an upright experimental reactor having an internal diameter of 15 cm. The lower layer comprised 1000 g of silver crystals having a particle size of from 1 to 2.5 mm, the middle layer comprised 65 g of silver crystals having a particle size of from 0.75 to 1 mm and the upper layer comprised 185 g of silver crystals having a particle size of from 0.2 to 0.75 mm.

A gas mixture comprising methanol, water and air was passed through a starting silver catalyst fixed bed which had been heated to 340° C. During the activation period of 23 hours, the amount was increased to 32 kg/h of methanol, 21.4 kg/h of water and 54 kg/h of air (final throughput). At the end of the activation period, the temperature in the fixed bed was 700° C. This flow was kept constant during the entire duration of the experiment. Subsequently, 0.42 mg of phosphorus per cm² of the cross-sectional area of the activated silver catalyst fixed bed was sprayed onto the surface of the latter in the form of a 3% strength by weight aqueous solution of $Na_4P_2O_7$, while the feeding in of the gas mixture was continued.

The reactor continued to be operated continuously and after a certain operating time of the reactor further amounts of phosphorus were applied to the phosphorus-doped silver catalyst fixed bed. The respective amounts (the cumulative amounts are indicated in the table), the yields of formaldehyde achieved and the time at which further phosphorus was applied, calculated from the time at which the phosphorus-doped silver catalyst fixed bed was produced by applying phosphorus for the first time to the activated silver catalyst fixed bed, are shown in the table.

Example 2 (For Comparison)

The starting silver catalyst fixed bed was produced as described in Example 1. Phosphorus in the form of pulverulent $Na_4P_2O_7$ was sprinkled onto its surface in an amount of 1.3 mg of phosphorus (calculated as elemental phosphorus) per cm² of cross-sectional area of the fixed bed. The catalyst fixed bed was heated to 360° C. and activated using the gas mixture indicated in Example 1 (same composition as in Example 1). The final throughput through the fixed bed could be achieved only after activation for 28 hours. The yield as a function of the operating time, from the time at which activation was complete (achievement of the final throughput), is shown in the table.

Example 3 (For Comparison)

The procedure described in Example 2 was repeated, but the temperature of the gas mixture introduced for activating the catalyst was only 340° C. The fixed bed was not able to be activated in this way.

| Example | Operating days | Amount of phosphorus [mg/cm²] | Yield [%] |
|---|---|---|---|
| 1 | 0 | 0.42 | 89.8 |
|   | 1 | 0.67 | 90.2 |
|   | 2 | 1.13 | 90.6 |
|   | 13 | 1.13 | 88.7 |
|   | 14 | 1.78 | 90.0 |
| 2(C) | 0 | 1.30 | 90.3 |
|   | 4 | 1.30 | 90.1 |

We claim:
1. A phosphorus-doped silver catalyst fixed bed obtained by
   I. arranging silver crystals obtained by electrolytic deposition of silver from an aqueous silver salt solution to form a starting silver catalyst fixed bed,
   II. producing an activated silver catalyst fixed bed from the starting silver catalyst fixed bed by passing through the latter, at from 150 to 800° C., a gas mixture comprising methanol and oxygen (gas mixture M), and
   III. bringing the activated silver catalyst fixed bed into contact with from 1 to 20,000 ppm by weight of phosphorus, based on the silver, in the form of a finely divided phosphorus compound having a melting point or decomposition temperature of more than 500° C. (phosphorus compound P).

2. A phosphorus-doped silver catalyst fixed bed as claimed in claim 1, wherein the starting silver catalyst fixed bed comprises one or more layers of silver crystals whose longest mean diameter is from 0.2 to 10 mm, and the total bed thickness is from 1 to 10 cm.

3. A phosphorus-doped silver catalyst fixed bed as claimed in claim 1, obtained by, in step III, sprinkling the phosphorus compound (P) in the form of a powder onto the activated silver catalyst fixed bed.

4. A phosphorus-doped silver catalyst fixed bed as claimed in claim 1, obtained by, in step III, impregnating the activated silver catalyst fixed bed with a solution of a phosphorus compound and evaporating the solution.

5. A phosphorus-doped silver catalyst fixed bed as claimed in claim 1, obtained by, for the activation of the starting silver catalyst fixed bed, arranging the latter in a fixed-bed reactor and continuously passing the gas mixture (M) through the reactor.

6. A phosphorus-doped silver catalyst fixed bed as claimed in claim 1, obtained by, for the production of the activated silver catalyst fixed bed, passing from 0.01 to 50 kg of methanol in the form of the gas mixture (M) per cm² of cross-sectional area of the starting silver catalyst fixed bed through the latter.

7. A process for preparing formaldehyde by oxidative dehydrogenation of methanol, which comprises passing the gas mixture (M) at from 150 to 800° C. through a phosphorus-doped silver catalyst fixed bed as claimed in claim 1.

8. A process as claimed in claim 7, wherein from 0.01 to 100 ppm by weight of phosphorus compound (P), based on the phosphorus-doped silver catalyst fixed bed, is applied to the latter per kg of methanol which is passed in the form of the gas mixture (M) through the phosphorus-doped silver catalyst fixed bed per cm² of the cross-sectional area of the latter, without interrupting the passing-through of the gas mixture (M).

9. A process for producing a phosphorus-doped silver catalyst fixed bed, which comprises I. arranging silver crystals obtained by electrolytic deposition of silver from an aqueous silver salt solution to form a starting silver catalyst fixed bed, II. producing an activated silver catalyst fixed bed from the starting silver catalyst fixed bed by passing through the latter, at from 150 to 800° C., a gas mixture comprising methanol and oxygen (gas mixture M), and III. bringing the activated silver catalyst fixed bed into contact with from 1 to 20,000 ppm by weight of phosphorus, based on the silver, in the form of a finely divided phosphorus compound having a melting point or decomposition temperature of more than 500° C. (phosphorus compound P).

* * * * *